United States Patent [19]

Allen et al.

[11] Patent Number: 5,457,055
[45] Date of Patent: Oct. 10, 1995

[54] DIAGNOSTIC METHOD FOR COBALAMIN DEFICIENCY

[75] Inventors: Robert H. Allen, Englewood; Sally P. Stabler, Denver, both of Colo.; John Lindenbaum, New York, N.Y.

[73] Assignee: The University of Colorado Foundation, Boulder, Colo.

[21] Appl. No.: 940,918

[22] Filed: Sep. 4, 1992

Related U.S. Application Data

[63] Continuation of Ser. No. 333,124, Apr. 3, 1989, abandoned, which is a continuation-in-part of Ser. No. 933,553, Nov. 20, 1986, Pat. No. 4,940,658.

[51] Int. Cl.$^6$ ............................ G01N 33/00; A01N 43/04
[52] U.S. Cl. ........................ 436/129; 436/161; 436/173; 436/175; 514/52
[58] Field of Search ............................ 436/74, 76, 92, 436/129, 161, 173, 174, 175, 177; 424/2; 514/52

[56] References Cited

U.S. PATENT DOCUMENTS 4,940,658  7/1990  Allen et al. .......................... 436/173 X

OTHER PUBLICATIONS

Lindenbaum, et al. (1988) "Neuropsychiatric Disorders Caused by Cobalamin Deficiency in the Absence of Anemia or Macrocytosis" New Eng. J. Med. 318:1720–1728.
Norman et al. (1982) "Cobalamin (Vitamin $B_{12}$) Deficiency Detection by Urinary Methylmalonic Acid Quantitation" Blood 59(6):1128–1131.
Lindenbaum et al. (1988) "New Assays for Cobalamin Deficiency: Getting Better Specificity" Laboratory Management 26:41–44.
Marcell et al. (1985) "Quantitation of Methylmalonic Acid and Other Dicarboxylic Acids in Normal Serum and Urine Using Capillary Gas Chromatography–Mass Spectrometry" Anal. Biochem. 150:58–66.
Stabler et al. (1986) "Assay of Methylmalonic Acid in the Serum of Patients with Cobalamin Deficiency Using Capillary Gas Chromatography–Mass Spectrometry" J. Clin. Invest. 77:1606–1612.
Leupold (1977) "Methylmalonacidurie" Klin. Wschr. 55:57–63.
Oberholzer et al. (1965) "Methylmalonic Aciduria" Arch. Dis. Childh. 42:492–504.
Morrow and Barness (1969) "Studies in a Patient With Methylmalonic Acidemia" J. Pediatr. 74(5):691–698.
Stabler et al. (1989) "Marked Elevation of Methylmalonic Acid (MMA) in Cerebral Spinal Fluid (CSF) of Patients With Cobalamin (Cbl) Deficiency" Clin. Res. 37(2):550A.
Sprinkle et al. (1969) "A Simple Method for the Determination of Methylmalonic Acid by Gas Chromatography" Clin. Chim. Acta 24:476–478.
Barness, L. A. (1967) "Vitamin $B_{12}$ Deficiency With Emphasis on Methylmalonic Acid as a Diagnostic Aid" Amer. J. Clin. Nutrition 20(6):573–577.

Primary Examiner—David A. Redding
Attorney, Agent, or Firm—Greenlee and Winner

[57] ABSTRACT

A method of diagnosing cobalamin deficiency in warm-blooded animals is described. In one embodiment, this method comprises the measurement of methylmalonic acid levels in cerebral spinal fluid to determine if such levels exceed normal range. A finding of elevated levels indicates a cobalamin deficiency. In another embodiment, the method comprises the measurement of methylmalonic acid levels in cerebral spinal fluid and serum. A finding that the ratio of methylmalonic acid in cerebral spinal fluid to that in serum is above normal is indicative of a cobalamin deficiency. Additionally, a method for assessing the effectiveness of cobalamin therapy is described. The effectiveness of therapy is assessed by determining whether cerebral spinal fluid levels of methylmalonic acid have returned to normal, or by determining whether the ratio of methylmalonic acid in cerebral spinal fluid to that in serum has returned to normal range. A method for distinguishing cobalamin deficiency from renal failure in warm-blooded animals having excessive serum MMA levels is also described. This method comprises determining the ratio of CSF MMA to serum MMA. A finding that the CSF MMA/serum MMA ratio is above normal or elevated is indicative of the presence of Cbl deficiency, whereas a finding that the CSF MMA/serum MMA ratio is below normal is indicative of renal failure.

6 Claims, No Drawings

DIAGNOSTIC METHOD FOR COBALAMIN DEFICIENCY

RELATEDNESS OF THE APPLICATION

The subject application is a continuation of co-pending U.S. Ser. No. 333,124, filed on Apr. 3, 1989 now abandoned, which is a continuation-in-part of U.S. Ser. No. 933,553, filed on Nov. 20, 1986, now issued as U.S. Pat. No. 4,940,658 on Jul. 10, 1990. Both U.S. Ser. No. 333,124 and U.S. Pat. No. 4,940,658 are incorporated herein by reference.

The research leading to this invention was, at least in part, funded by U.S. government agencies. The U.S. has certain rights in this invention.

FIELD OF THE INVENTION

This invention relates to a method of diagnosis of cobalamin deficiency in warm-blooded animals, particularly humans by the measurement of the level of methylmalonic acid in cerebral spinal fluid of such animals.

BACKGROUND OF THE INVENTION

Cobalamin (Cbl) or vitamin $B_{12}$ deficiency, usually the result of disruption of the absorption of cobalamin, can lead to life-threatening hematological and neuropsychiatric abnormalities. Accurate and early diagnosis of cobalamin deficiency is important since proper treatment with cobalamin results in complete reversal of the hematologic symptoms. Early diagnosis is especially important in order to avoid potentially incapacitating, irreversible neurologic damage. Administration of exogenous cobalamin always stops the progression of neuropsychiatric abnormalities, almost always leads to significant improvements in such symptoms and frequently leads to their complete correction. Early diagnosis is often difficult since the clinical signs of Cbl deficiency can result from a variety of other disorders. It has generally been taught that Cbl deficiency should be suspected in individuals with significant anemia, displayed for example in decreased hematocrit or hemoglobin, with macrocytic red blood cells (i.e., mean cell volume (MCV) generally greater than 100 fl), or in individuals having the neurologic symptoms of peripheral neuropathy and/or ataxia. Anemia associated with Cbl deficiency has been described as typically severe with hemoglobin $\leq 8$ g % or hematocrit <25% and the size of the red blood cells is described as greatly increased to levels >110 fl. (See, for example, Babior and Bunn (1983) in *Harrison's Principles of Internal Medicine* (Petersdorf et al., eds.) McGraw-Hill Book Co., New York; Lee and Gardner (1984) In *Textbook of Family Practice, 3rd Ed.* (Rakel, ed.) Saunders & Co., Philadelphia). While it was well recognized that individuals with Cbl deficiency could display neurologic disorders in the absence of anemia, such situations were believed to be exceptional and rare (Beck (1985) in *Cecil Textbook of Medicine, 17th Ed.* (Wyngaarden and Smith, eds.) W. B. Saunders, Philadelphia, p. 893–900; Babior and Bunn (1987) in *Harrison's Principles of Internal Medicine, 11th Ed.* (Braunwald et al., eds.) McGraw-Hill, New York pp.1498–1504; Walton (1985) *Brain's Diseases of the Nervous System, 9th Ed.* Oxford University Press, Oxford, UK). The neurologic symptoms of Cbl deficiency have often been considered to be late manifestations of the disease most typically occurring after the onset of anemia or if they occur first, are soon to be followed with onset of anemia (Woltmann (1919) Am. J. Med. Sci. 157:400–409; Victor and Lear (1956) Am. J. Med. 20:896–911). These symptoms have also been thought to often result from inappropriate therapy with folic acid (Conley and Krevans (1951) New Eng. J. Med. 245:529–531).

Lindenbaum et al. (1988) New Eng. J. Med. 318:1720–1728 have recently reported that neuropsychiatric disorders resulting from Cbl deficiency occur commonly in the absence of anemia and elevated MCV. They reported that a large percentage (28%) of the Cbl deficient patients displaying neuropsychiatric abnormalities in their study had no anemia or macrocytosis or had only minor hematologic abnormalities. Further, they reported that a much wider spectrum of neuropsychiatric symptoms can result from Cbl deficiency, see also Lindenbaum et al. (1988) Laboratory Management 26:41–44.

The serum cobalamin assay has been essentially the only laboratory assay generally available for use in determining if a patient is Cbl deficient. Presently preferred cobalamin assays are radiodilution assays which use pure or purified intrinsic factor as the binding protein (see: Kolhouse et al. (1978) New Eng. J. Med. 299:785–792). This assay has been criticized as frequently giving low Cbl values in patients who lack any evidence of Cbl deficiency. It has been suggested (Schilling et al. (1983) Clin. Chem. 29:582–583) that this assay may frequently give false positives showing low serum Cbl levels in individuals who are not Cbl deficient.

It has long been known that methylmalonic acid (MMA) is excreted in increased amounts in the urine of most patients with Cbl deficiency (see, for example, Cox and White (1962) Lancet ii:853–856; Norman et al. (1982) Blood 59:1128–1131). In Cbl deficiency, reduced levels of adenosyl-Cbl result in decreased activity of L-methylmalonyl-coenzyme A (CoA) mutase and a concomitant increase in intracellular levels of L-methylmalonyl-CoA. D-methylmalonyl-CoA, resulting from transformation of the L-isomer by D,L-methylmalonyl-CoA racemase (Stabler et al. (1985) Arch. Biochem. Biophys. 241:252–264), is cleaved to CoA and MMA by D-methylmalonyl-CoA hydrolase which has been recently characterized (Kovachy et al. (1983) J. Biol. Chem. 258:11415–11421). MMA is then released into blood in unknown amounts and is excreted in the urine. About 70% of the MMA in blood is metabolized to unknown products via as yet undefined pathways and only about 30% is excreted in the urine. Although it has been suggested that Cbl deficiency can be detected by urine MMA analysis (Norman et al. (1982) Blood 59:1128–1131), in practice urine MMA has rarely been measured and has been deemed rarely necessary in patients suspected of being Cbl deficient, since it has been taught that accurate diagnosis can be based on the presence and degree of anemia and macrocytosis and by the measurement of serum cobalamin levels (see: Beck (1983) in *Hematology, 3rd Ed.* (Williams et al., eds.) McGraw-Hill, New York, pp. 434–465, Beck (1985) supra).

Recently, a comparison of MMA levels in urine and serum of normal subjects and Cbl deficient subjects has become possible with the development of a sensitive capillary gas chromatography-mass spectrometry method for quantitation of MMA and other dicarboxylic acids (Marcell et al. (1985) Anal. Biochem. 158:58–66; Stabler et al. (1986) J. Clin. Invest. 77:1606–1612; Lindenbaum et al. (1988) New Eng. J. Med. supra; Allen et al. U.S. Patent application Ser. No. 933,553, filed Nov. 20, 1986, which is incorporated by reference herein). Prior to these reports MMA had not been detected in serum of normal subjects. Levels of serum MMA of 26,000 to 340,000 ng/ml had previously been reported in patients with inborn errors of metabolism involving the synthesis of adenosyl-Cbl or the adenosyl-Cbl-dependent enzyme, L-methylmalonyl-CoA mutase (see: Rosenberg (1983) in *The Metabolic Basis of Inherited Disease* (Goldstein and Brown, eds.) McGraw-Hill, New York p.474–497). Urine MMA levels in these patients were reported to be 10- to 100-fold higher than serum levels. Marcell et al. reported that MMA in the serum and urine of normal subjects ranged from 19–76 ng/ml and 270–7190 ng/ml, respectively. Stabler et al. reported that serum MMA levels of clinically confirmed Cbl deficient patients ranged from 55 to 22,300 ng/ml, with 69 of 73 of such patients having serum MMA levels above the normal range. It was also reported that there was a positive correlation between serum MMA levels and the presence of neurologic abnormalities in these patients. Lindenbaum et al. reported that serum MMA levels were elevated above normal levels in 36 of 37 Cbl deficient patients who displayed neuropsychiatric abnormalities in the absence of anemia or other severe hematologic abnormalities. Further, it is suggested that high serum MMA levels which return to normal after cobalamin therapy provide a useful confirmation of the presence of Cbl deficiency.

SUMMARY OF THE INVENTION

It is an object of this invention to provide a method of diagnosing the presence of Cbl deficiency in warm-blooded animals, in particular humans, which comprises the measurement of MMA levels in cerebral spinal fluid (CSF). This invention is based on the discoveries that MMA can be detected and quantitated in CSF; in non-Cbl deficient subjects MMA levels in CSF are higher than those in serum; and in subjects with Cbl deficiency the levels of MMA in CSF are often elevated to a higher degree than they are in serum. A finding of above normal, elevated levels of MMA in CSF is indicative of the presence of Cbl deficiency. A finding of elevated levels of MMA in CSF of animals, particularly humans, having neuropsychiatric abnormalities indicates that these abnormalities are likely the result of Cbl deficiency. Measurement of MMA levels in CSF is particularly useful in the diagnosis of Cbl deficiency in subjects who do not have the hematologic abnormalities usually associated with Cbl deficiency or in those subjects who display only minor hematologic abnormalities.

In an alternative embodiment this invention provides an method of diagnosing Cbl deficiency which comprises the measurement of MMA levels in CSF and serum to allow a determination of the ratio of CSF MMA to serum MMA. A finding that the CSF MMA/serum MMA ratio is above normal or elevated is indicative of the presence of Cbl deficiency. A finding that the CSF MMA/serum MMA ratio is normal, in the presence of elevated levels of serum and CSF MMA does not exclude a diagnosis of Cbl deficiency.

It is a further object of this invention to provide a method for assessing the effectiveness of cobalamin therapy by measuring the levels of MMA in CSF after administration of exogenous cobalamin. The lowering of CSF MMA levels to the normal range is indicative of the effectiveness or adequacy of cobalamin therapy. Alternatively, the effectiveness or adequacy of cobalamin therapy can be assessed by determining the CSF MMA/serum MMA ratio in subjects after treatment with cobalamin. The lowering of the CSF MMA/serum MMA ratio to within the normal range and concomitant lowering of CSF MMA levels to the normal range is indicative of effective therapy. Either of these alternative methods can be applied to assess the amount of cobalamin required and the frequency of administration necessary to achieve effective therapy.

An improved method for treatment of Cbl deficiency involves the combination of administration of exogenous cobalamin employing existing treatment methods, in which dosages and in which the method and frequency of administration of cobalamin, or functional equivalents of cobalamin, are well-known in the art, with assessment of the effect of treatment on the level of MMA in CSF or on the ratio of CSF MMA/serum MMA. After administration of initial cobalamin treatment, MMA levels in CSF or in both serum and CSF are quantitated. These measurements are used to assess if the initial mode of cobalamin treatment is adequate. If it is not, the mode of treatment is modified and MMA levels in serum and/or CSF are again measured after modified treatment has been administered to assess the effect of the modifications. Treatment is modified and assessed with MMA measurements until an effective mode of treatment is attained which results in the lowering of CSF MMA to normal levels. Yet another object of the invention is to provide a method for distinguishing cobalamin deficiency from renal failure in warm-blooded animals, particularly humans, having excessive serum MMA levels, which comprises the measurement of MMA levels in CSF and serum to allow a determination of the ratio of CSF MMA to serum MMA. A finding that the CSF MMA/serum MMA ratio is above normal or elevated is indicative of the presence of Cbl deficiency, whereas a finding that the CSF MMA/serum MMA ratio is below normal is indicative of renal failure.

DETAILED DESCRIPTION OF THE INVENTION

A deficiency of cobalamin can cause a number of hematological, neuropsychiatric and other abnormalities. Hematologic abnormalities associated with Cbl deficiency include among others, anemia; macrocytosis; neutropenia; thrombocytopenia; elevated serum LDH or bilirubin; decreased serum haptoglobin; neutrophil hypersegmentation, macroovalocytes, anisocytosis or poikilocytosis in blood smears; hypercellular or megaloblastic morphology in bone marrow. Neuropsychiatric abnormalities associated with Cbl deficiency include among others paresthesia; ataxia; memory loss; weakness; altered mood or behavior; decreased manual dexterity; fatigue; pain in the extremities; urinary or fecal symptoms (incontinence, etc.); hallucinations; confusion; obtundation; impotence; decreased vision; suicide and anorexia. Other symptoms associated with Cbl deficiency include glossitis; infertility; gastrointestinal symptoms; hyperpigmentation; orthostatic hypotension and weight loss. Cbl deficient patients may have only certain hematologic effects, some only certain neuropsychiatric abnormalities, others a mixture of both and others none at all. None of these symptoms or abnormalities is specific for Cbl deficiency, since they may be caused by a variety of other diseases.

The measurement of serum cobalamin levels has been used in the diagnosis of Cbl deficiency. The normal human range of serum cobalamin is about 200–900 pg/ml. Below normal serum cobalamin levels are indicative of Cbl deficiency. However, it has been taught that Cbl deficient subjects will not only have below normal levels of serum cobalamin but that these levels will be significantly depressed below about 100 pg/ml (see: Babior and Bunn (1983) supra; Lee and Gardner (1984) supra; Beck (1985) supra; Beck (1983) supra). Cobalamin assays have been criticized as giving frequent false positive results, as noted above, and recently Lindenbaum et al. (1988) New Eng. J. Med. supra have reported two clinically confirmed Cbl deficient patients having serum cobalamin levels in the normal range. The presence of Cbl deficiency is confirmed by the observation of amelioration of clinical symptoms after administration of cobalamin treatment. The measurement of serum cobalamin levels can not be employed to assess the adequacy of cobalamin treatment, since cobalamin levels will always be elevated or at least normal after parenteral injections of cobalamin, regardless of whether the subject is Cbl deficient or not. It has been reported that the measurement of serum MMA is useful in the diagnosis of Cbl deficiency (Lindenbaum et al. (1988) New Eng. J. Med. supra and Stabler et al. (1986) supra), with elevated levels of MMA present in serum of most Cbl deficient patients examined. Serum MMA levels will correctly detect Cbl deficiency in at least some patients in whom the serum cobalamin level does not. In contrast to serum cobalamin levels, the effectiveness of cobalamin therapy can be assessed by measuring the change in serum MMA levels after administration of cobalamin.

It has now been discovered that MMA can be detected and quantitated in human cerebral spinal fluid. It has been found that in normal subjects CSF levels of MMA are higher than serum levels. It has also been found that the levels of MMA in CSF are elevated above normal in subjects that are clinically confirmed to be Cbl deficient and further that in many such subjects CSF levels of MMA are elevated to a greater extent than they are in serum. For example, it was found that the relative values of the organic acid succinic acid (an isomer of MMA) in CSF and serum were quite different than the relative levels of MMA in CSF and serum. The mean levels of succinic acid in CSF (1003 nM) was much lower than in serum (3603 nM).

The level of MMA in cerebral spinal fluid was not predictable from a knowledge of the level of MMA in serum. CSF MMA need not be in diffusional equilibrium with serum MMA. It was also not predictable that the level of MMA in CSF of normal subjects would be higher than in normal serum. Further, it was not predictable that the level of CSF MMA would be elevated in Cbl deficient subjects and it was not predictable that in many such patients that CSF MMA/serum MMA ratio would be significantly greater than in non-Cbl deficient subjects.

This work provides the first measurement of the levels of CSF MMA in normal subjects. The determination of what is normal allowed the demonstration that CSF MMA levels are elevated in Cbl deficient patients. Prior to this work, MMA has been measured in CSF in only a very few instances in patients having severe inborn metabolic errors of cobalamin metabolism or L-methylmalonyl mutase. These patients are characterized as excreting high levels of MMA in urine. In review articles (Rosenberg (1983) supra and Leupold (1977) Klin. Wschr.55:57–63) describing these inborn disorders, it is stated that levels of CSF MMA and serum MMA in these patients are elevated and about equal. In Oberholzer et al. (1967) Arch. Dis. Childh. 42:492–504 one measurement of CSF MMA and serum MMA in one patient with such an inborn error was reported giving about equal MMA values in CSF and serum of 186,000 ng/ml and 183,000 ng/ml, respectively. Morrow and Barnes (1969) J. Pediatr. 74:691–698 also report a single measurement of MMA in CSF and serum of one such patient, giving values of 30,000 ng/ml for serum and 110,000 ng/ml for CSF. Serum MMA levels in this patient were reported to vary considerably from a high in times of illness of 300,000 ng/ml to a low of 10,000 ng/ml when the patient was well.

In a study of 25 human subjects without Cbl deficiency (see data in Table 1), MMA levels in CSF ranged from 194 to 545 nM (23 to 64 ng/ml), with a mean value of 300 nM (35 ng/ml). Serum MMA levels in these same subjects ranged from 50–229 nM (5.9 to 27 ng/ml), with a mean value of 135 nM (16 ng/ml). The ratio of CSF MMA/serum MMA ranged from 1.29 to 5.64 with a mean value of 2.49.

TABLE 1

Levels of Methylmalonic Acid and Succinic Acid in Serum and Cerebral Spinal Fluid (CSF) of Normal Subjects

| Patient | Methylmalonic Acid (nmol/l) | | | Succinic Acid (nmol/l) | | |
| --- | --- | --- | --- | --- | --- | --- |
| | Serum | CSF | CSF/Serum | Serum | CSF | CSF/Serum |
| 1 | 185 | 481 | 2.60 | 1707 | 979 | 0.57 |
| 2 | 105 | 203 | 1.93 | 3818 | 555 | 0.15 |
| 3 | 99 | 293 | 2.96 | 3815 | 676 | 0.18 |
| 4 | 196 | 386 | 1.97 | 5101 | 2053 | 0.40 |
| 5 | 163 | 261 | 1.6 | 6639 | 1855 | 0.28 |
| 6 | 50 | 237 | 4.74 | 2736 | 528 | 0.19 |
| 7 | 213 | 395 | 1.85 | 2202 | 480 | 0.22 |
| 8 | 229 | 409 | 1.79 | 9122 | 2521 | 0.28 |
| 9 | 112 | 285 | 2.54 | 4709 | 2162 | 0.46 |
| 10 | 84 | 317 | 3.77 | 5419 | 3234 | 0.60 |
| 11 | 169 | 424 | 2.51 | 4910 | 2184 | 0.44 |
| 12 | 98 | 319 | 3.26 | 3128 | 653 | 0.21 |
| 13 | 133 | 545 | 4.10 | 2052 | 502 | 0.24 |
| 14 | 90 | 253 | 2.81 | 2711 | 670 | 0.25 |
| 15 | 164 | 292 | 1.78 | 2961 | 841 | 0.28 |
| 16 | 147 | 224 | 1.52 | 2905 | 315 | 0.11 |
| 17 | 163 | 208 | 1.28 | 5023 | 569 | 0.11 |
| 18 | 122 | 230 | 1.89 | 2569 | 526 | 0.20 |
| 19 | 143 | 194 | 1.36 | 3243 | 574 | 0.18 |
| 20 | 61 | 344 | 5.64 | 2544 | 899 | 0.35 |
| 21 | 169 | 227 | 1.34 | 2936 | 749 | 0.26 |
| 22 | 89 | 207 | 2.33 | 1906 | 379 | 0.20 |
| 23 | 96 | 245 | 2.55 | 2383 | 599 | 0.25 |
| 24 | 220 | 281 | 1.28 | 2775 | 215 | 0.08 |
| 25 | 82 | 241 | 2.94 | 2752 | 368 | 0.13 |
| MEAN: | 135 | 300 | 2.49 | 3603 | 1003 | 0.26 |
| MINIMUM: | 50 | 194 | 1.28 | 1707 | 215 | 0.08 |
| MAXIMUM: | 229 | 545 | 5.64 | 9122 | 3234 | 0.60 |

In a study of three patients with elevated serum MMA due to chronic renal failure, CSF MMA levels (651, 539, and 349 nM) were within the normal range in two instances and in all three cases lower than the respective serum levels (1110, 564 and 563 nM). In all cases, the CSF MMA/serum MMA ratios were lower than normal (0.59, 0.96 and 0.62, respectively).

A demented patient (patient A, Example 3) with Cbl deficiency who had a significantly low serum cobalamin level of 31 pg/ml and hematologic symptoms consistent with Cbl deficiency (hematocrit=9% and MCV=116 fl) was found to have a CSF MMA level of 358,000 nM, a serum MMA level of 34,500 nM and a CSF MMA/serum MMA ratio of 10.38. The MMR in CSF is clearly elevated as is the MMA level in serum; however, the elevation of MMA in CSF (approx. 1000-fold) is much greater than the elevation of MMA in serum (approx. 200-fold).

A second patient (patient B, Example 3) with severe spinal cord abnormalities due to nitrous oxide inactivation of cobalamin who had a normal serum cobalamin level of 275 pg/ml and no severe hematologic signs of Cbl deficiency (hematocrit =47% and MCV=101 fl) was found to have a CSF MMA level of 166,000 nM. a serum level of MMA of 12,300 nM and a CSF MMA/serum MMA ratio of 13.50. Again the CSF level of MMA is clearly above normal, as is the serum MMA level, and MMA is elevated to a greater extent in CSF compared to serum. The effect of cobalamin therapy on serum and CSF MMA levels in this patient were examined. One week after cobalamin therapy was started, patient B had an elevated serum cobalamin level, as would be expected, and showed little change in hematocrit (49%) and a fall in MCV to 95 fl. MMA in CSF and serum had decreased to 26,700 nM and 2970 nM, with a CSF E/serum MMA ratio of 8.99, all still above normal levels. Some improvement in neurologic symptoms was observed. Reexamination of patient B after another seven weeks of more intense cobalamin therapy showed an elevated serum cobalamin level of 2,900 pg/ml, but the MMA levels in CSF (199 nM) and serum (84 nM) and the CSF MMA/serum MMA ratio of 2.37 were within the normal range. The lowering of MMA to normal levels was accompanied by significant improvement in neurologic symptoms in this patient.

A third patient, patient C, exhibited paresthesia and weight loss. There were no strong hematologic indications of Cbl deficiency. Serum cobalamin level was below normal (120 pg/ml) although not severely depressed. The levels of both serum and CSF MMA were elevated (4314 nM and 14,880 nM, respectively), which is indicative of the presence of Cbl deficiency. In contrast to Patients A and B, the CSF MMA/serum MMA ratio was 3.44, within the normal range. Cbl deficiency in this patient has not as yet been clinically confirmed. These results suggest, however, that a finding that the CSF MMA/serum MMA ratio is normal with concomitant elevation of CSF and serum MMA does not exclude a diagnosis of Cbl deficiency.

For application to the present invention any method for quantitation of MMA in CSF or serum can be employed, as long as the method employed is quantitatively reproducible and is sensitive enough to detect MMA at the levels encountered in serum and CSF. The method employed must be capable of distinguishing elevated from normal levels of MMA. The range of normal MMA levels in serum and CSF is determined, for example, as described in Example 2, by quantitation of these levels in a set of normal, non-Cbl deficient subjects. MMA is suitably assayed, for example, by the methods of Norman et al. (1982) supra or Marcell et al. (1985) supra. The MMA assay employing GC/MS provided herein is preferred. In the preferred method, a sample is combined with a known amount of a internal standard which comprises a known amount of MMA labelled with a stable isotope marker, such as deuterium. The sample containing an unknown amount of unlabelled MMA and a known amount of labelled MMA internal standard is prepared for analysis, by partial purification and derivatization, if necessary, and the amount of labelled and unlabelled MMA in the sample is determined, for example, by mass spectrometric analysis. The amount of MMA in the original sample is then calculated based on the amount of internal standard added to the sample. CSF samples are preferably subjected to partial purification by extraction and HPLC as described in Marcell et al. (1985) supra or more preferably by extraction and silica gel column chromatography, as described in Example 1.

As briefly mentioned above, a preferred method for detecting cobalamin deficiency in a human involves determining methylmalonic acid concentration by gas chromatography-mass spectrometry. More particularly, this preferred method for detecting cobalamin deficiency in a human involves assaying cerebral spinal fluid of said human to determine if methylmalonic acid concentration therein exceeds a predetermined range, wherein excessive methylmalonic acid is indicative of a cobalamin deficiency, and wherein said method comprises the steps of:

(a) adding a known amount of an internal standard to said cerebral spinal fluid, said internal standard comprising methylmalonic acid labeled with a stable isotope marker, (b) adjusting the pH of said cerebral spinal fluid to about 1, (c) extracting said acidified fluid with ether, (d) applying said ether extract to a silica gel column which has been washed and equilibrated with ether, (e) washing said applied extract on said column with methanol, (f) eluting a fraction containing methylmalonic acid and internal standard by applying a mixture of about 4N $NH_4OH$ in methanol to said column containing said applied extract, (g) collecting said eluted fraction and derivatizing methylmalonic acid and internal standard contained therein, and (h) determining methylmalonic acid concentration in said cerebral spinal fluid by gas chromatography-mass spectrometry quantitation of methylmalonic acid and internal standard in said derivatized eluted fraction.

An alternative preferred method for detecting cobalamin deficiency in a human involves assaying cerebral spinal fluid of said human to determine if methylmalonic acid concentration therein exceeds a predetermined range, wherein excessive methylmalonic acid is indicative of said cobalamin deficiency, said method comprising the steps of:

(a) adding a known amount of an internal standard to said cerebral fluid, said internal standard comprising methylmalonic acid labeled with a stable isotope marker, (b) adjusting the pH of said fluid of step (a) to about 12, (c) extracting said basic cerebral spinal fluid of step (b) with ether and discarding said ether extract, (d) adjusting the pH of said extracted cerebral spinal fluid of step (c) to about 1, (e) extracting the acidic cerebral spinal fluid of step (d) with ether and collecting said ether extract, (f) injecting said extract of step (e) onto a high performance liquid chromatography anion exchange system having a mobile phase consisting of about 0.05M $KH_2PO_4$—$H_3PO_4$ at pH 2, (g) collecting a fraction containing methylmalonic acid and internal standard, (h) adjusting the pH of said fraction of step (g) to about 1, (i) extracting said acidified fraction of step (h) with ether, (j) derivatizing methylmalonic acid and internal standard in said ether fraction of step (i), and (k) determining methylmalonic acid concentration in said cerebral spinal fluid by quantitating derivatized methylmalonic acid and internal standard in said derivatized fraction of step (j) by gas chromatograph-mass spectrometry.

The invention is further illustrated and exemplified by the following non-limiting examples.

EXAMPLES

Example 1: Representative Assay for Methylmalonic Acid

An improvement of the method of Marcell et al. (1985) supra describing MMA analysis in serum and urine has been employed for measurement of MMA in CSF.

A volume of 50 μl of $H_2O$ containing known amounts of internal standards, i.e. 100–200 ng of [methyl-$^2H_3$] MMA and 1000–2000 ng of [1,4-$^{13}C_2$] succinic acid, was added to 400 μl of CSF or serum. The pH of the samples was then adjusted to about 1 by adding 1 ml of 0.6N HCl and the acidified samples were mixed. The samples were then extracted with diethyl ether by addition of 9 ml of ether, followed by vortexing (15 min). The ether layer (leaving about 1 cm of ether on top of the water layer) was collected and applied to a polypropylene column (0.8×4.0 cm) containing 0.8–1.0 ml of silica gel (70–230 mesh, Cat. No. S-2509, Sigma Chemical Co, St. Louis, Mo.) which had been washed and equilibrated with ether. The column was then washed (3×3 ml) with methanol and the washes discarded. Sample was eluted from the column with 2 ml of 4N $NH_4OH$ in methanol into a 12×75 mm culture tube. Methanol was then removed (to dryness) from the samples in a Speed Vac vacuum concentrator (Savant Instruments, Inc. Hicksville, N.Y.). Sample residue was then taken up in 300 μl of methanol and transferred to a polypropylene autosampler vial. Methanol was removed (to dryness) from the samples in the vacuum concentrator. Dicarboxylic acids in the samples were derivatized to t-butyldimethylsilyl esters by adding 20μl of acetonitrile and 10 μl of N-methyl-N-(t-butyldimethylsilyl)trifluoroacetamide to each vial. The vials were sealed with aluminum-seal, Teflon-silicone septa caps, vortexed and allowed to stand at 40° C. for 30 min.

About 2 μl of the derivatized sample was injected onto the capillary column of a Hewlett-Packard (Palo Alto, Calif.) 5890 gas chromatograph-mass spectrometer (GC/MS) via a 7673a autosampler injector. Sample resolution was achieved on a Durabond DB-1 fused silica capillary column (30 m×0.25 mm i.d., 0.25 μm film thickness) from J & W Scientific, Inc. (Rancho Cordova, Calif.). The GC/MS was operated under standard autotune conditions with an injection port temperature of 250° C. and a column head pressure of 22 psi. The capillary column was equilibrated at 80° C., and approximately 1.0 min. after sample injection was increased to 300° C. at a rate of 30° C./min.

Data were collected from 6.0 to 7.5 min using the selected ion monitoring mode. The following [M-57]+ ions were monitored using a 10 ms dwell time for each: MMA, m/z 289.2; [methyl-$^2H_3$] -MMA m/z 292.2; succinic acid, m/z 289.2; [1,4-$^{13}C_2$]succinic acid, m/z 291.2. MMA was quantitated by dividing the integrated area of the m/z 289.2 peak that eluted at approximately 6.8 min (the exact elution times were determined daily employing standards) by the integrated area of the m/z 292.2 peak that eluted at the same time, and then multiplying by the amount of [methyl-$^2H_3$] MMA standard (typically 100–200 ng) added to each sample. Succinic acid was quantitated in the same manner utilizing the m/z 289.2 and m/z 291.2 peaks that eluted at approximately 7.2 min and multiplying by the amount of [1,4-$^{13}C_3$]succinic acid standard added to each sample (typically 1000–2000 ng). The integrated areas of the peaks for the internal standards, i.e. the m/z 292.2 and m/z 291.2 peaks eluting at about 6.8 and 7.2 min, respectively, were corrected for the amounts contributed to them by endogenous MMA and succinic acid as a result of naturally occurring isotope abundance. These corrections, which were determined for unenriched methylmalonic and succinic acids on a daily basis, were as follows: (1) the m/z 292.2 peak from MMA (eluting at about 6.8 min) was approximately 1.9% of the MMA m/z 289.2 peak and (2) the m/z 291.2 peak from succinic acid (eluting at about 7.2 min) was approximately 10.8% of the area of the succinic acid m/z 289.2 peak.

The partial sample purification, employing silica gel chromatography, utilized in this procedure was necessary because of the complex mixture of organic acids found in serum and CSF and because of the relatively low concentrations of MMA present. Extractions with various organic solvents followed by further purification with small anion-exchange or reverse-phase columns were found to be unsatisfactory for this application. HPLC using an anion-exchange resin, as was described in Marcell et al. (1985) supra, was found useful for the separation of the dicarboxylic acids under study from other compounds present in serum. The silica gel partial purification procedure for CSF and serum samples, described hereinabove, represents an improvement over the previously employed HPLC method resulting in more efficient sample cleanup and more accurate MMA measurements.

De Jong et al. (1980) Biomed. Mass Spectrom. 7:359–364 have described derivatization of dicarboxylic acids with a mixture of t-butyldimethylchlorosilane/N,N-dimethylformamide/imidazole (Applied Science Laboratories, Inc., State College, Pa.). This method for production of t-butyldimethylsilyl derivatives was found to be unsatisfactory for quantitative work due to marked variations in the degree of derivatization achieved and due to the relative instability of the derivatives obtained. It was found that the pH of the reaction mixture as described by de Jong et al. was approximately 1, and that this resulted in the hydrolysis of the newly formed t-butyldimethylsilyl esters of the dicarboxylic acids. The imidazole present in the reaction mixture is apparently unable to completely scavenge the HCl produced in the reaction. Addition of acid scavengers, such as pyridine, did not fully correct the problem. In contrast, the derivatization procedure employing N-methyl-N-(t-butyldimethysilyl)trifluoroacetamide, described above, resulted in high-yield, reproducible derivatization of dicarboxylic acids.

The molecular weights of methylmalonic and succinic acid are 118. The molecular weight of a particular t-butyldimethylsilyl derivative is equal to the molecular weight of the dicarboxylic acid plus 228 (two t-butyldimethylsilyl groups). Molecular ion peaks, [M]+, representing the entire derivative were not observed. The major peak observed, representing 35–45% of the sum of all peaks observed in the m/z range of 100–400, in each case was the [M-57]+ fragment due to loss of $C_4H_9$. Smaller peaks, about 3–6% of the amount of the [M-56]+peaks, at [M-15]+due to the loss of a $CH_3$ group were also observed.

The capillary column employed in the GC/MS separation gave a complete separation for the derivatives having the same molecular weight, i.e., the derivatives of MMA and succinic acid were completely separated.

Samples of human CSF and serum appeared to contain no substances, as examined by GC/MS, that might interfere with the use of [methyl-$^2H_3$]methylmalonic and [1,4-$^{13}C_2$] succinic acids as internal standards for quantitation in the GC/MS procedure.

Methylmalonic and succinic were purchased from Sigma Chemical Company (St. Louis, Mo.). [Methyl-$^2H_3$]MMA (>99%, via custom synthesis) and [1,4-$^{13}C_2$]succinic acid (>99%) were purchased from Merck Sharpe & Dohme Isotopes (Montreal, Canada). [Methyl-14C]MMA (via custom synthesis) and [1,4 -$^{14}C_2$]succinic acid were purchased from New England Nuclear Corp. (Boston, Mass.). N-Methyl-N(t-butyldimethylsilyl) trifluoroacetamide was obtained from Pierce Chemical Co. (Rockford, Ill.).

Example 2: Determination of Methylmalonic Acid Levels in CSF of Normal Subjects

Cerebral spinal fluid and serum samples were collected from a set of 25 subjects displaying no clinical signs of Cbl deficiency. These subjects had normal serum MMA levels, did not have low serum cobalamin levels and had normal renal function as assessed by normal blood urea nitrogen (BUN) and creatinine levels. CSF and simultaneously collected serum samples were assayed for MMA and succinic acid as described in Example 1. The results of these assays are given in Table 1. The mean value for MMA in CSF in these 25 subjects were found to range from 194 to 545 nM, with a mean value of 300 nM. This is significantly greater than the level of MMA found in serum of these subjects, which ranged from 50–229 nM with a mean of 135 nM. The mean ratio of MMA in CSF to MMA in serum was 2.22. In contrast, the level of succinic acid in CSF was much lower than that in serum. The mean ratio of succinic acid in CSF to succinic acid in serum was 0.28, with the level of succinic acid in normal CSF ranging from 215–3234 nM (mean =1003 nM) and that in serum ranging from 1707 to 9122 (mean =3603 nM).

The values determined for serum MMA and succinic acid in this set of normal subjects are lower than found previously in Marcell et al. (1985) supra. It is believed that his difference is due to the improved purification of samples prior to GC/MS analysis, as described above.

Example 3: Measurement of MMA in CSF of Patients Displaying Neuropsychiatric Abnormalities Patient A. A 77-year-old woman was admitted with a history of dementia of unknown duration, having been found at home in a confused state. She was disoriented and incoherent. Vibration sense was markedly impaired in her ankles and feet. The hematocrit was 9%, MCV 116 fl., reticulocyte count 0.9%, WBC 1800/µl and platelet count 16,000/µl. Blood smear showed hypersegmented neutrophils and macroovalocytes. Serum LDH 1400 U/l; serum Cbl, 31 pg/ml and serum folate, 1.5 ng/ml. Serum homocysteine was 142.3 nM and serum MMA, 34,509 nM. CSF MMA was 357,606 nM. The CSF was otherwise normal. The ratio of MMA in CSF to that in serum was approximately 10.

The patient was treated with blood transfusions, vitamin $B_{12}$ and folic acid. Three weeks later she was reevaluated neurologically and was found to be alert, well oriented and able to carry on a coherent conversation. Vibration sense remained impaired in the legs. She was sent to a nursing home.

Patient B. A 39-year-old dentist experienced three episodes in 1980, 1986 and 1988 of a neurological disorder characterized by progressively more severe paresthesia and unsteady gait with eventual inability to walk. He was hospitalized for each episode. Loss of vibration and position sense, spasticity and weakness in all four extremities and hyperactive reflexes were present on each of the three occasions. The third recurrence of symptoms was accompanied by memory loss, and rambling and disconnected conversation. A diagnosis of multiple sclerosis was made and he was treated in 1981 and 1986 with corticosteroid hormones and bed rest, with striking recovery over 1–2 month periods. In 1986 he admitted for the first time to episodic nitrous oxide abuse preceding the neurologic symptoms but the diagnosis was still considered to be multiple sclerosis.

When admitted in November 1988, the hematocrit was 49%, MCV 101 fl., WBC 6,200 and platelet count 327,000. LDH was 194 units. Serum Cbl was 275 pg/ml on admission (repeat on same specimen 285 pg/ml) and 200 pg/ml 10 days later. Serum folate was 13.5 and 6.7 ng/ml. Blood smears showed increased numbers of 5-lobed and rare 6-lobed neutrophil and a few macroovalocytes. Antibodies to intrinsic factor were not present in serum. Serum MMA was 12,327 nM and serum HCYS 81.3 µM. Cerebrospinal fluid was normal except for an MMA level of 166,000 nM. Thus, the CSF E/serum MMA =13.4. In serum specimens obtained 9 and 10 days later, the MMA was 22,414 and 34,154 nM and HCYS 73.8 and 86.0 µM. The patient again admitted to recent heavy nitrous oxide abuse along with codeine and Valium.

The patient was readmitted in December 1988 after taking 100 µg of vitamin $B_{12}$ by mouth 4–5 times a day for one week. He reported some neurologic improvement and was able to walk unaided but with a spastic gait, and complained of paresthesia. Slight improvement in position sense and muscle strength were noted but the neurologic examination remained markedly abnormal. The hematocrit was 49% and MCV 95 fl. Blood smear was unchanged. Serum Cbl was 430 pg/ml and serum folate 11.0 ng/ml. Serum HCYS was 30.5 µM and MMA, 2966 nM. CSF MMA was 26,662 nM, with CSF MMA/serum MMA lowered to 9.0. More intense therapy with parenteral vitamin $B_{12}$ was begun. He received 1 mg once a week for three weeks and subsequently 1 mg every other day for one month as well as 4–8 mg by mouth daily.

He was readmitted in early February 1989. His symptoms were markedly improved, although mild paresthesia was still present. The neurologic examination showed further improvement, although vibration sense impairment, spastic gait, extensor plantar reflexes and a positive Romberg sign were still present. The hematocrit was 45% and MCV 92 fl. Blood smear was now normal. Serum Cbl was 2,900 pg/ml and serum folate 9.6 ng/ml. Serum HCYS (10.2 µM) and MMA (84 nM) were normal, as was CSF MMA (199 nM) and CSF-MMA/serum MMA (2.4). It is now believed that the patient never had multiple sclerosis, and that all the neurological abnormalities were due to inaction of cobalamin by nitrous oxide.

Patient C. A 63-year-old woman complained of numbness and pain in the right leg, burning in both feet and a 25-pound weight loss over the past year. There was a history of latent syphilis treated 6 months ago with penicillin. Physical examination was unremarkable. The hematocrit was 38%, MCV 101 fl., WBC 7000 µl, and platelet count 265,000 µl. Serum Cbl was 120 pg/ml, serum folate 6.9 ng/ml, serum MMA 4314 nM and serum HCYS 36.7 nM. CSF was normal except for an MMA level of 14,880 nM (CSF/serum MMA= 3.44). Antibodies to intrinsic factor were absent from serum. The response of this patient to cobalamin therapy has not yet been determined.

It will be appreciated by those skilled in the art that functionally equivalent alternatives exist for certain materials, techniques and procedures employed in the methods specifically described herein. Persons skilled in the art are able to select and use appropriate alternatives to achieve the desired result, as described herein. Any such alternatives now available to the art or that in the future become available to the art are considered to be within the spirit and scope of this invention.

We claim:

1. A method for detecting cobalamin deficiency in a human by assaying the levels of methylmalonic acid in the cerebral spinal fluid and serum of said human to determine the ratio of methylmalonic acid in cerebral spinal fluid to that in serum, to assess whether said ratio exceeds a predetermined range, wherein an excessive ratio is indicative of cobalamin deficiency, and wherein said method comprises the steps of:

(a) adding a known amount of an internal standard to said cerebral spinal fluid, said internal standard comprising methylmalonic acid labeled with a stable isotope marker, (b) adjusting the pH of said cerebral spinal fluid to about 1, (c) extracting said acidified fluid with ether, (d) applying said ether extract to a silica gel column which has been washed and equilibrated with ether, (e) washing said applied extract on said column with methanol, (f) eluting a fraction containing methylmalonic acid and internal standard by applying a mixture of about 4N $NH_4OH$ in methanol to said column containing said applied extract, (g) collecting said eluted fraction and derivatizing methylmalonic acid and internal standard contained therein, (h) determining methylmalonic acid concentration in said cerebral spinal fluid by gas chromatography-mass spectrometry quantitation of methylmalonic acid and internal standard in said derivatized eluted fraction, (i) repeating steps (a) through (h) using said serum of said human to determine methylmalonic acid concentration in said serum, and (j) determining the ratio of methylmalonic acid in cerebral spinal fluid to that in serum, to assess whether said ratio exceeds normal range, wherein excessive ratio is indicative of cobalamin deficiency.

2. A method of assessing the adequacy of cobalamin therapy in a human having cobalamin deficiency which comprises assaying cerebral spinal fluid and serum of said human according to the method of claim 1 after administration of said cobalamin therapy, to determine the ratio of methylmalonic acid in cerebral spinal fluid to that in serum, to assess whether said ratio has returned to a predetermined range, wherein return to said predetermined range is indicative of the adequacy of the therapy.

3. An improved method for treatment of cobalamin deficiency by administration of exogenous cobalamin in humans wherein the improvement comprises the assessment of the adequacy of cobalamin therapy by assaying cerebral spinal fluid and serum according to the method of claim 1 after administration of said exogenous cobalamin to determine the ratio of methylmalonic acid in cerebral spinal fluid to that in serum, to assess whether said ratio has returned to a predetermined range, wherein return to said predetermined range is indicative of adequacy of said therapy.

4. A method for detecting cobalamin deficiency in a human by assaying the levels of methylmalonic acid in the cerebral spinal fluid and serum of said human to determine the ratio of methylmalonic acid in cerebral spinal fluid to that in serum, to assess whether said ratio exceeds a predetermined range, wherein an excessive ratio is indicative of cobalamin deficiency, and wherein said method comprises the steps of:

(a) adding a known amount of an internal standard to said cerebral fluid, said internal standard comprising methylmalonic acid labeled with a stable isotope marker, (b) adjusting the pH of said fluid of step (a) to about 12, (c) extracting said basic cerebral spinal fluid of step (b) with ether and discarding said ether extract, (d) adjusting the pH of said extracted cerebral spinal fluid of step (c) to about 1, (e) extracting the acidic cerebral spinal fluid of step (d) with ether and collecting said ether extract, (f) injecting said extract of step (e) onto a high performance liquid chromatography anion exchange system having a mobile phase consisting of about 0.05M $KH_2PO_4$—$H_3PO_4$ at pH 2, (g) collecting a fraction containing methylmalonic acid and internal standard, (h) adjusting the pH of said fraction of step (g) to about 1, (i) extracting said acidified fraction of step (h) with ether, (j) derivatizing methylmalonic acid and internal standard in said ether fraction of step (i), (k) determining methylmalonic acid concentration in said cerebral spinal fluid by quantitating derivatized methylmalonic acid and internal standard in said derivatized fraction of step (j) by gas chromatograph-mass spectrometry, (l) repeating steps (a) through (k) using said serum of said human to determine methylmalonic acid concentration in said serum, and (m) determining the ratio of methylmalonic acid in cerebral spinal fluid to that in serum, to assess whether said ratio exceeds normal range, wherein excessive ratio is indicative of cobalamin deficiency.

5. A method of assessing the adequacy of cobalamin therapy in a human having cobalamin deficiency which comprises assaying cerebral spinal fluid and serum of said human according to the method of claim 4 after administration of said cobalamin therapy, to determine the ratio of methylmalonic acid in cerebral spinal fluid to that in serum, to assess whether said ratio has returned to a predetermined range, wherein return to said predetermined range is indicative of the adequacy of the therapy.

6. An improved method for treatment of cobalamin deficiency by administration of exogenous cobalamin in humans wherein the improvement comprises the assessment of the adequacy of cobalamin therapy by assaying cerebral spinal fluid and serum according to the method of claim 4 after administration of said exogenous cobalamin to determine the ratio of methylmalonic acid in cerebral spinal fluid to that in serum, to assess whether said ratio has returned to a predetermined range, wherein return to said predetermined range is indicative of adequacy of said therapy.

* * * * *